United States Patent [19]

D'Alelio

[11] 4,131,730

[45] Dec. 26, 1978

[54] MODIFIED POLYAMIC ACID FROM AMINOPHTHALIC ACID ANHYDRIDE AND DIANHYDRIDE

[76] Inventor: Gaetano F. D'Alelio, South Bend, Ind.

[21] Appl. No.: 821,405

[22] Filed: Aug. 3, 1977

Related U.S. Application Data

[62] Division of Ser. No. 576,469, May 12, 1975, Pat. No. 4,064,113, which is a division of Ser. No. 370,286, Jun. 15, 1973, abandoned.

[51] Int. Cl.$^2$ .................. C08G 69/12; C08G 69/48

[52] U.S. Cl. .................................... 528/327; 528/310; 528/311; 528/331

[58] Field of Search ................................. 260/78 A

[56] References Cited

U.S. PATENT DOCUMENTS 3,951,922  4/1976  Richter et al. .................... 260/78 A

*Primary Examiner*—Harold D. Anderson
*Attorney, Agent, or Firm*—Walter J. Monacelli

[57] ABSTRACT

Processes are described for the preparation of substantially pure aminophthalic anhydrides and for polymerizing these monomers to unmodified and modified improved polyamic acid and polyimides.

15 Claims, No Drawings

MODIFIED POLYAMIC ACID FROM AMINOPHTHALIC ACID ANHYDRIDE AND DIANHYDRIDE

This is a division of application Ser. No. 576,469 filed May 12, 1975, now U.S. Pat. No. 4,064,113, which in turn is a division of prior application Ser. No. 370,286, filed May 12, 1975, now abandoned, but for which a continuing application was filed July 25, 1975, Ser. No. 598,929, for which Patent No. 3,979,416 was granted on Sept. 7, 1976.

PRIOR ART

A synthesis of 4-aminophthalic anhydride was reported originally in JACS 30, 1135 (1908). The properties described for this aminophthalic anhydride cast doubts on its identity. Later, J. Brandt in J. Prakt. Chem., Vol. 7, Ser. 4, 163–172 (1958) established that it had not been synthesized; this later reference describes inadequately the synthesis of 4-aminophthalic anhydride in low yields by the reduction of 4-nitrophthalic anhydride. Brandt also describes the formation of a polyamic acid of aminophthalic anhydride, followed by its isolation under hydrolyzing conditions, as a low molecular weight product. U.S. Pat. No. 3,450,678 describes a process for preparing film-forming polyamideacids from aminophthalic anhydrides by reaction in an inert solvent; it does not describe the synthesis of the aminophthalic anhydrides.

THE DISCLOSURE

This invention relates to the aminophthalic anhydrides of the formula $H_2NC_6Y_3(CO)_2O$ and to polymers derived therefrom, wherein $C_6$ represents the benzene ring to which is attached one $NH_2$ group, and an anhydride group in the 1,2- positions, and Y represents hydrogen or a halogen selected from the class of bromine, fluorine and chlorine. These aminophthalic anhydrides can be formulated also as

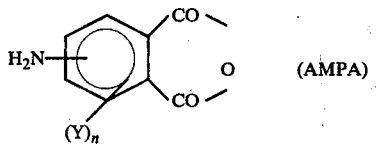

(AMPA)

wherein Y represents a halogen selected from the class of F, Br and Cl, and $n$ is an integer having a value of zero to three. Illustrative examples of AMPA are
3-aminophthalic anhydride,
4-fluoro-, 3-aminophthalic anhydride,
5-bromo-, 3-aminophthalic anhydride,
6-chloro-, 3-aminophthalic anhydride,
4-fluoro-, 3-aminophthalic anhydride,
3-fluoro-, 4-aminophthalic anhydride,
5-fluoro-, 4-aminophthalic anhydride,
6-fluoro-, 4-aminophthalic anhydride,
4,5-dichloro-, 3-aminophthalic anhydride,
4,5-dibromo-, 3-aminophthalic anhydride,
4,6-dichloro-, 3-aminophthalic anhydride,
3,5-dichloro-, 4-aminophthalic anhydride,
3,6-dichloro-, 4-aminophthalic anhydride,
5,6-dichloro-, 4-aminophthalic anhydride,
4,5,6-trichloro-, 3-aminophthalic anhydride,
3,5,6-tribromo-, 4-aminophthalic anhydride,
3,5,6-trichloro-, 4-aminophthalic anhydride,
3,5,6-trifluoro-, 4-aminophthalic anhydride,
3-chloro-, 5-bromo-, 6-fluoro-, 4-aminophthalic anhydride, etc.

One objective of the present invention is a method of preparing substantially pure aminophthalic anhydrides in relatively high yields by the catalytic reduction of the corresponding precursor nitro compounds. Another objective is to prepare polymers directly by the reduction of the nitro compounds, $O_2NC_6Y_3(CO)_2O$, in solution. A still further objective is to prepare modified, improved novel polymers of the aminophthalic anhydrides by a process which comprises modifying the polymerization of said anhydride by coreactive compounds selected from the class of aromatic di-primary amines, $Ar'(NH_2)_2$, and aromatic dicarboxylic anhydrides, $Ar[(CO)_2O]_2$, both of which are more fully described hereinafter. It is a further purpose of the invention to prepare the modified polymers by coreaction of the diamine or dianhydride modifiers with the isolated aminophthalic anhydrides or during the course of the catalytic reduction of the precursor nitrophthalic anhydrides. Still another objective of this invention is to prepare modified polymers having either terminal amino, $-NH_2$ groups or dianhydride, $>(CO)_2O$, groups which have greater utility than the unmodified polymers of the aminophthalic anhydrides. Other objectives will become apparent as the description of the invention proceeds.

I have discovered that the pure aminophthalic anhydrides, AMPA, can be prepared by catalytically hydrogenating the corresponding nitrophthalic anhydrides, $O_2NC_6H_3(CO)_2O$, in a non-reactive organic solvent at a concentration of no higher than about 30% by weight of anhydride at a temperature in the range of about 0° C to about 27° C, and thereafter recovering the aminophthalic anhydride by precipitation. I have established that evaporation of the solvent is an unsatisfactory method of isolation, if high yields of high purity AMPA are to be achieved. Also, I have found that when organic compounds are used as precipitants for AMPA in the organic solvent used in the synthesis, the yields are very low, as for example, when hexane or benzene are added to solutions of AMPA in dioxane or dimethylacetamide respectively.

In the process of this invention, a non-reactive organic solvent which is water-soluble is the preferred solvent since precipitation of the aminophthalic anhydride occurs by the addition of the solution to water refrigerated to a temperature of about −30° C to about 20° C, preferably from about 0° C to about 5° C, without hydrolysis of the anhydride. Below 0° C, the precipitant-water obviously is in the form of ice, which preferably is crushed or in the form of snow. At higher than about 20° C, the risk of the hydrolysis of the anhydride to the diacid is high. The precipitated AMPA is readily removed by filtration or by centrifugation and dried in vacuo without heat. By this process, I have obtained the pure aminophthalic anhydrides in yields in excess of 90% and approaching theoretical values, and in high purity. For example, I have prepared the previously undisclosed substantially pure 4-aminophthalic anhydride, of a melting point of 207°–208° C, and characterized it by elemental analysis, infrared spectroscopy and by formation of known derivatives.

The ratio of the volume of water to the non-reactive water-soluble organic can be varied over a wide range depending particularly on the nature of the organic solvent and the concentration of the AMPA dissolved therein. Preferably, the amount of water is determined experimentally and selected to afford the maximum yield of AMPA, preferably a yield above 95% of AMPA. Generally, the amount of water will vary from about ¼ to 5-10 times the volume of the solvent. A preferred operating range is from about 1 to 5 volumes of water per volume of solvent.

In contrast to this process, I have observed that if the catalytic hydrogenation is performed in an inert organic solvent, and isolation of the AMPA is attempted by evaporation of the solvent, even without heat, part or all of the AMPA is converted to an oligomer or polymer, and, if any monomer is isolable after concentration, the yield or the purity or both are low. I have also discovered that if the concentration of the nitrophthalic is higher than about 30% by weight in the non-reactive solvent, or if the temperature exceeds about 25° C by about 5°-10° C, the yield of AMPA is substantially reduced. Typical suitable water-soluble organic solvents for hydrogenation of the nitrophthalic anhydrides from which AMPA can be isolated by precipitation with water are N,N-dimethylacetamide (DMAC), N,N-dimethylformamide (DMF), N,N-diethylformamide, N,N-dimethylmethoxyacetamide, N-methyl-caprolactam, N,N-diethylacetamide, dimethyl sulfoxide, N-methyl-2-pyrrolidone, tetramethylurea, pyridine, dimethylsulfone, hexamethylphosphoramide, formamide, N-methylformamide, butyrolactone, N-formylpiperidine, N-formyl-pyrrolidone, dioxane, tetrahydrofurane, etc., or mixtures of such solvents with each other or with minor amounts of solvents having limited solubility in water, such as nitromethane, tetramethylenesulfone, etc.

I have further discovered that I can prepare a polyamic acid of AMPA having an inherent viscosity of at least 0.30 dl/g as 0.5% solution in DMAC at 30° C directly in solution by a preferred modification of the process of this invention which comprises catalytically hydrogenating at 30°-100° C a 30-70% solution of AMPA in an organic solvent in which the polymer is also soluble. When the temperature of hydrogenation is above about 35° C, preferably an insoluble, inorganic dehydrating agent is present in sufficient quantity to inactivate the water formed in the reduction of the —$NO_2$ group to an —$NH_2$ or water formed by the cyclization of some of the hemiamic structures, which water is otherwise capable of hydrolyzing the amide linkages in the chain and causing a marked reduction in inherent viscosity. The hydrolytic effect of water increases with temperature and the presence of dehydrating agent in the system is more critical than at lower temperatures, at which it can be used to assure high intrinsic viscosity. For these same reasons, dehydrating agents may be used, if desired, when the process of the invention is used to prepare monomeric AMPA. Usually, I prefer to operate at temperatures at which the inorganic dehydrating agent is not required critically. Typical inorganic dehydrating agents are, magnesium sulfate, sodium sulfate, calcium sulfate, barium sulfate, alumina, molecular sieves, etc.

I have also discovered that I can produce modified polymers of AMPA during the course of the hydrogenation of the nitrophthalic anhydride under the conditions described hereinabove, when the reduction is performed in the presence of the coreactive compounds, $O(OC)_2Ar(CO)_2O$ and $H_2NAr'NH_2$ such as are used to modify the polymerization of preformed monomeric AMPA.

As coreactive anhydride modifiers to be used in the practice of this invention, any organic aromatic-type compound is suitable which has two dicarboxylic acid anhydride groups in which the CO moieties in the anhydride groups are ortho-disposed to each other, $O(OC)_2Ar(CO)_2O$, the only requirement in these compounds being that the anhydride groups are attached directly to the aromatic ring. This Ar can be the tetravalent nucleus from a single aromatic ring such as benzene, toluene, xylene, etc., or fused aromatic rings such as naphthalene, anthracene, phenanthrene, etc., or aromatic-heterocyclics such as pyridine, quinoline, quinoxaline, etc., as well as a multiplicity of such aromatic nuclei linked together directly to each other or by means of —O—, —S—, —CO—, —$SO_2$—, —$CR_2$—,

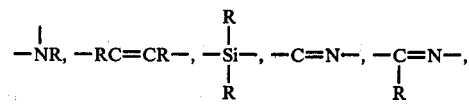

etc., linkages in which R represents hydrogen or a hydrocarbon group containing one to twelve carbon atoms such as —$CH_3$, —$C_6H_{12}$, —$C_6H_5$, —$C_{12}H_{25}$, or by ester linkages such as by —COO—, or by imide linkages such as

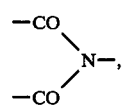

and —CONR—, or by quinoxaline linkages, etc. In each case both >$(CO)_2O$ groups are attached to six-membered aromatic rings, such as for example, to the structures:

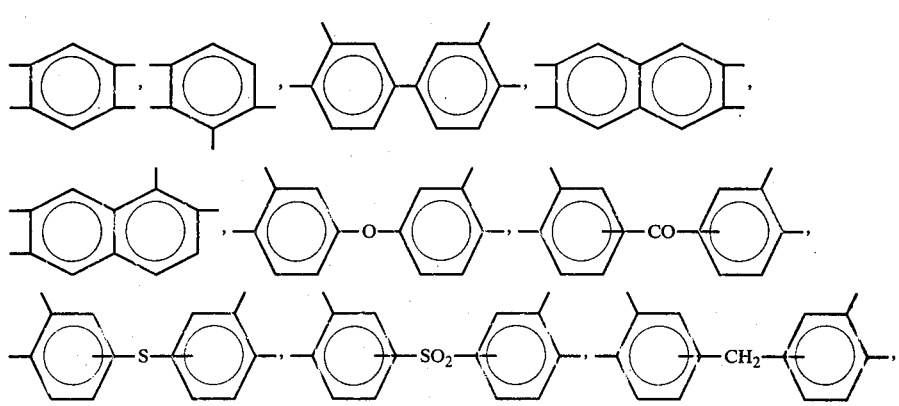

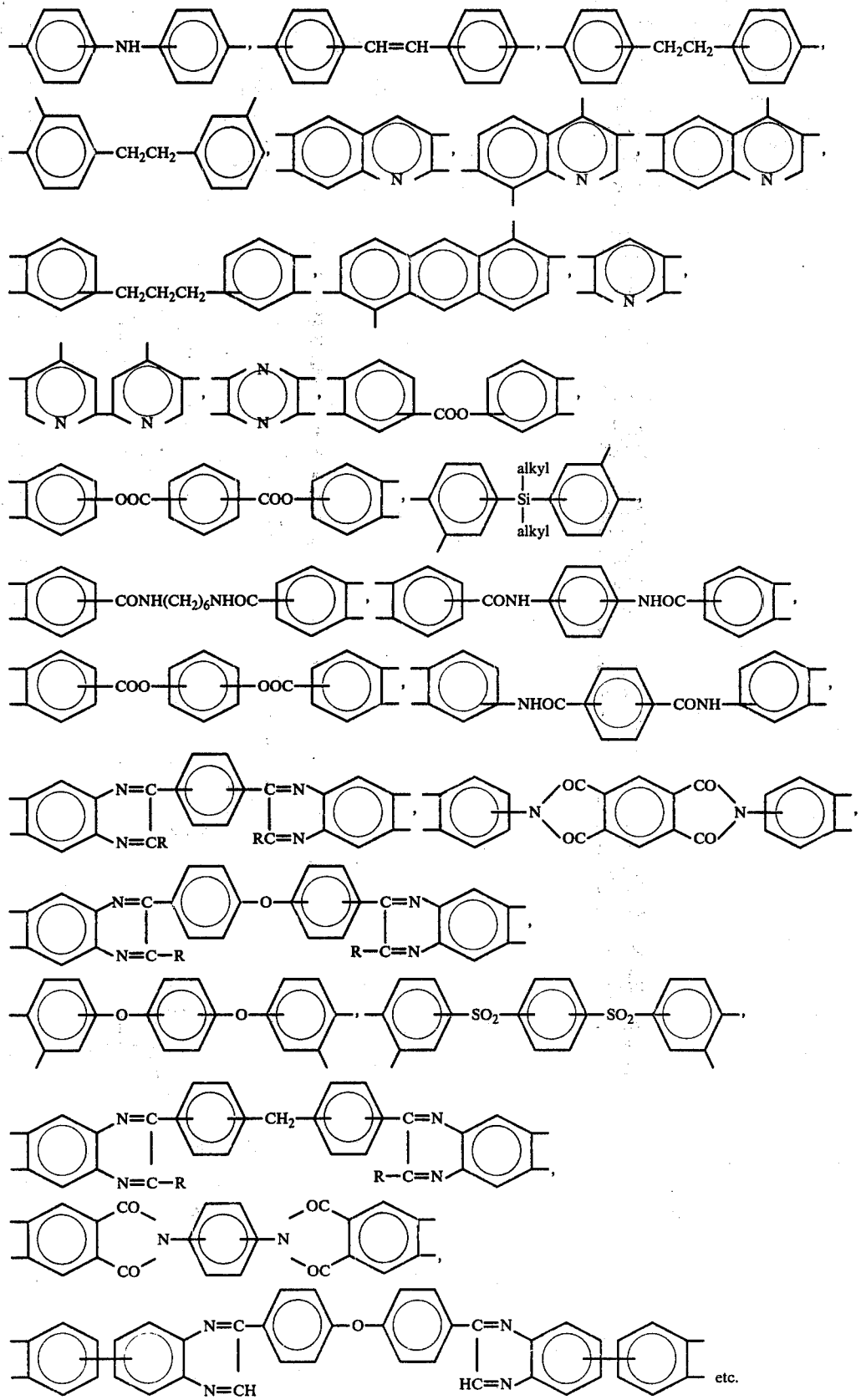
The substituents not occupied in the structures by >(CO)₂O groups are occupied by hydrogen or any of the substituents which normally are found on aromatic-type structures such as halogen, for example, Cl and Br, nitrile, alkoxy, aryloxy, hydrocarbon, etc., with the hydrocarbon and hydrocarbonoxy portions having no more than 10 carbon atoms, but hydrogen and halogen are preferred.

For reasons of economy and availability, the $O(OC)_2Ar(CO_2O$ compounds can also be oligomeric or polymeric such as are derived by the reaction of $n + 1$ moles of monomeric dianhydride with $n$ moles of the aromatic diamine, $Ar(NH_2)_2$, having the general formula $O(OC)_2Ar(CO)_2[NAr'N(OC)_2Ar(CO)_2]_nO$, so that the anhydride groups are termini in the structure wherein the value of $n$ is at least one and as high as 10 or 20. A typical example of such a dianhydride is

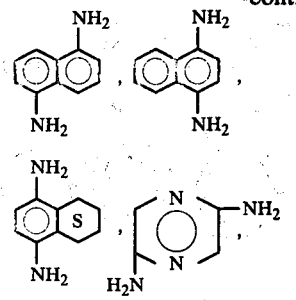

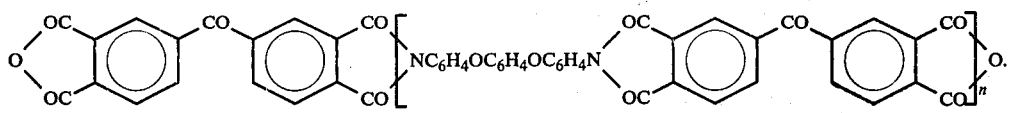

Thus, in the case of pyromellitic anhydride, $O(OC)_2C_6H_2(CO)_2O$, the molecular weight is of the order of 220 and in case of the anhydride end-capped oligomer of an $n$ value of 10, the molecular weight is of the order of 6200. For reasons of availability and economy,

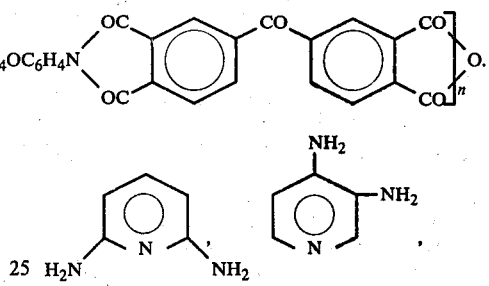

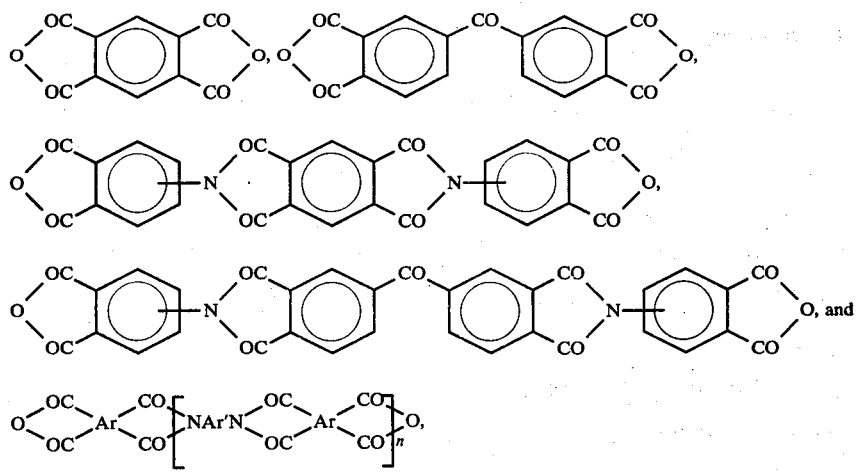

wherein $n$ represents 1 to 10, are preferred compounds for use in the practice of this invention. The synthesis of such anhydride-terminated oligomers is illustrated below in examples 27-30.

In the diamine compounds, $Ar'(NH_2)_2$, used as modifiers in the practice of this invention, $Ar'$ is the divalent moiety corresponding to Ar in $O(OC)_2Ar(CO)_2O$ except that two additional valencies in Ar are occupied by hydrogen, R, halogen, nitrile, and OR, but hydrogen and halogen are preferred. Some representative diamines are

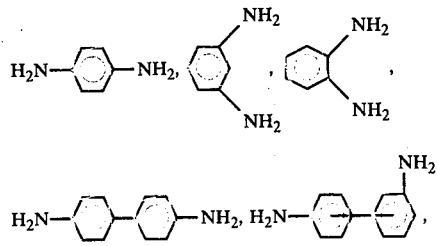

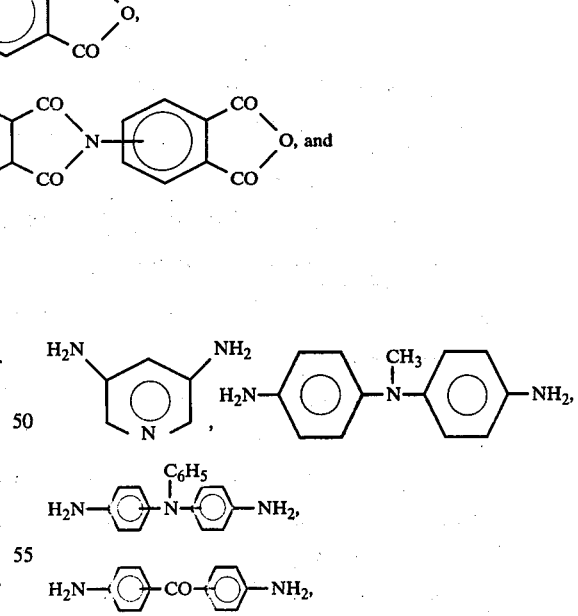

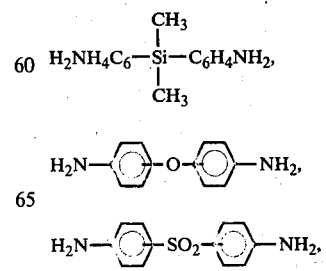

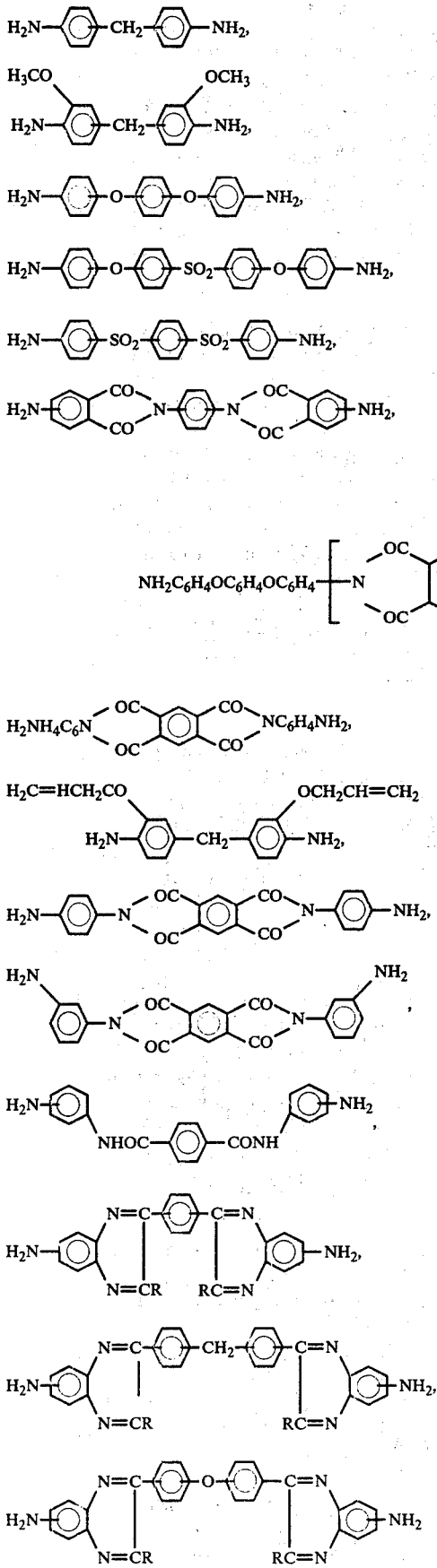

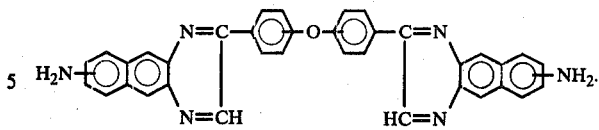

The Ar'(NH$_2$)$_2$ compounds can also be oligomeric or polymeric such as are derived by the reaction of $(n+1)$ moles of aromatic diamine and $n$ moles of O(OC)$_2$Ar(CO)$_2$O having the general formula

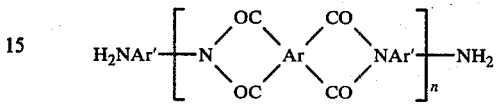

so that the NH$_2$ groups are terminal in the structure wherein $n$ has a numerical value of at least one and as high as ten or twenty. A typical example of such a diamine is

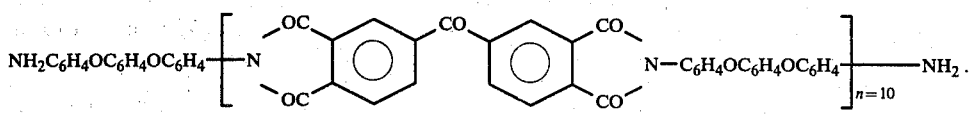

The synthesis of such arylamino-terminated oligomers is illustrated below in examples 23–26.

In the case of C$_6$H$_4$(NH$_2$)$_2$ the molecular weight is of the order of 108 and that of the above diamino end-capped oligomer in which $n=10$, is of the order of 6200.

Thus, the amount of the dianhydride or diamine modifier used in the practice of this invention may be varied over a wide range of concentration, due to the wide range in molecular weights of these modifiers. For example, when the molecular weight of the modifier is low, of the order of 100 to 300 or 500, the molar ratio of these modifiers to AMPA may be in the range of 1 to 100 to 1 to 1000, and when the molecular weight is in the range of 2500, the mole ratio of the modifier to AMPA may be as low as 1 to 10 and up to 1 to 1000; and when the molecular weight is in the range of 5000, the mole ratio may be in the range of 1 to 5 to 1 to 5000.

In the embodiment of this invention in which the nitrophthalic anhydride is reduced to AMPA and polymerized in the course of the reduction, the solvent used is an organic solvent in which the polymer as well as the monomer is substantially soluble. This requirement is met substantially by the list of solvents given heretofore hereinabove from N,N-dimethylacetamide to N-formylpyrrolidone, inclusive, as well as by pyridine,
tetramethylenesulfoxide,
pentamethylenesulfone,
N,N-bis(cyanomethyl)formamide,
N,N'-diformyl-piperazine,
N,N-dimethylcyanamide,
m-cresol,
xylenol,
N,N-dimethylaniline,
N,N,N',N'-tetramethyl-alpha-ethylmalonamide,
N,N,N',N'-tetramethylglutaramide,
N,N,N',N'-tetramethylsuccinamide,
thiobis-(N,N-dimethylacetamide), bis(N,N-dimethylcarbamylmethyl) ether,
N,N,N',N'-tetramethylfumaramide,
methylsuccinonitrile,
1,2,3-tricyanopropane,
alpha-ethylsuccinonitrile,
succinonitrile,
N,N-dimethylcyanoacetamide,
N,N-dimethyl-beta-cyano-propionamide,
dimethylester of methane disulfonic acid,
diethylester of ethane-1,2-disulfonic acid,
bis-(cyanomethyl)-sulfone,
1,2-diethiocyanopropane,
bis-(thiocyanomethyl) ether,
beta-thiocyanoisobutyronitrile,
malonitrile,
N-acetyl-2-pyrrolidone, etc.

The solvents can be used alone, in combination of solvents, or in combination with poorer solvents such as ketones, such as methyl ethyl ketone; nitroalkanes such as nitroethane, nitropropane, etc., or non-solvents such as minor amounts of benzene, benzonitrile, dioxane, xylene, toluene, trimethyl benzene and cyclohexane, which can also act as azeotroping agents to remove water of condensation.

The following examples illustrate the practice of this invention. All percentages, here as well as throughout the specification, are by weight unless otherwise specified.

EXAMPLE 1

In a 100-ml round-bottom flask equipped with an inlet tube for deoxygenated nitrogen, a gas outlet tube, a thermometer extending to the bottom of the flask and an electric heating mantle, was placed 21.1 g of 4-nitrophthalic acid and the apparatus was flushed with nitrogen. The mass was heated under a slow flow of nitrogen for 4 hours at 165°–170° C, and then allowed to cool to room temperature. The crude product was added to toluene, heated to reflux, and filtered while hot. The filtrate was cooled to 0° C, the solid precipitate recovered by filtration, recrystallized from chloroform and dried to constant weight at 35° C in a vacuum oven, to yield 11.08 g of 4-nitrophthalic anhydride, m.p. 123°–124° C, whose percent elemental analysis of C, 49.81; H, 1.53; N, 7.22 is in excellent agreement with the theoretical values.

EXAMPLE 2

A mixture of 21.1 g of 4-nitrophthalic acid and 50.0 g of acetic anhydride were heated at reflux for 6 hours, following which the acetic acid was removed by distillation at atmospheric pressure. The excess acetic anhydride was removed by distillation at 15 mm Hg pressure with the flask temperature not exceeding 120° C, leaving a quantitative yield of crude 4-nitrophthalic anhydride, m.p. 114°–116° C. The product was recrystallized from chloroform to afford a 93% yield of product, m.p. 123°–124° C, identical to that of Example 1.

EXAMPLE 3

3-Nitrophthalic anhydride was prepared from 3-nitrophthalic acid and acetic anhydride by the same procedure given for its 4-nitro isomer in Example 2. The yield of recrystallized product was 17.85 g (92.5%); m.p. 163°–164° C, whose percent elemental analysis of C, 49.79; H, 1.57; N, 7.22 is in excellent agreement with the theoretical values.

EXAMPLE 4

Phthalic anhydride was nitrated by the procedure described by Miller in Ann. 208, 223 (1881) and by Bogert in JACS, 28, 617 (1906) to afford an approximately 50:50% mixture of 3- and 4-nitrophthalic acid which was treated with acetic anhydride by the procedure of Example 2, resulting in a 91.6% yield of the recrystallized mixture of anhydrides, having an m.p. range of 102°–106° C. The percent elemental analysis of C, 49.81; H, 1.57; N, 7.22 is in excellent agreement with the theoretical values of C, 49.74; H, 1.55; N, 7.25.

EXAMPLE 5

In this example, 4-nitrophthalic anhydride was reduced by the procedure given by Brandt in J. Prakt. Chem., Vol. 7, Ser. 4, 167 (1958). Within the reaction chamber of a hydrogenation apparatus, in 30 ml of dioxane, there was dissolved 3.0 g of 4-nitrophthalic anhydride, to which was added 0.5 g of Raney Nickel (W. R. Grace No. 28 Raney Active Nickel Catalyst in Water, Type W-2, which was washed first with methanol and then with dioxane). Then the apparatus was pressured to 250 psi with hydrogen and an exotherm occurred during the first hour of the hydrogenation, which raised the temperature from 24° C to 36° C. The hydrogenation was terminated at the end of 8 hours. The solution was filtered to remove the nickel and divided into three 10-ml portions.

Portion A

This 10-ml portion was processed by Bandt's procedure and was added to 100 ml of 0.5 N HCl solution, yielding a flocculent precipitate which was isolated by filtration and redissolved in 100 ml of 2% $NH_3$ solution and reprecipitated by 0.5 N HCl solution, isolated and dried. There was obtained 0.47 g of a white solid, which did not melt when heated to 300° C; its equivalent weight by titration with 0.1 N NaOH was 183.3 and its infrared spectrum was identical to that of an authentic sample of 4-aminophthalic acid of an equivalent weight of 181.1. Its analytic percent values were C, 53.1; H, 3.79; N, 7.65; it had an inherent viscosity of 0.5 g in 100 ml of dimethylacetamide at 25° C of 0.09 dl/g.

The elemental analysis reported by Brandt (p. 167) of percent C, 53.3; H, 3.8; N, 7.6 for his product as a hydrate of 4-aminophthalic anhydride is in good agreement with the calculated values of percent C, 53.04; H, 3.90; N, 7.73 for 4-aminophthalic acid.

Portion B

The second 10-ml portion was concentrated by evaporation of the dioxane at 25° C without heating at 10 mm Hg pressure to approximately 3 ml of a viscous mass, after which a sample of approximately 1 ml was spread as a thin layer on a glass plate and placed in an oven at 110° C for 10 hours to eliminate residual dioxane (B.P. 101° C) and there was obtained a film whose infrared spectrum showed bands for —COOH in the 3000 $cm^{-1}$ region and for —CONH— in the 1660 $cm^{-1}$ region.

The remaining material of approximately 2 ml was washed with benzene and dried in a vacuum oven to yield 0.69 g of resin whose inherent viscosity of 0.5 g in 100 g of dimethylacetamide at 25° C was 0.23 dl/g.

Portion C

The third 10-ml portion was isolated by precipitation by adding it slowly with rapid stirring to 150 ml of benzene to yield a yellow precipitate which was removed by filtration and dried in vacuo at room temperature. Its inherent viscosity was 0.24 dl/g and it was soluble in dimethylacetamide from which films were cast on glass plates by drying at 115° C for 24 hours.

Brandt's procedures show that with Raney Nickel catalyst at room temperature and a 10% solution of 4-nitrophthalic anhydride in a solvent such as dioxane, which does not react with anhydride groups, reduction of the amine group occurs which is accompanied by an exotherm inducing the polycondensation to a hemiamic acid polymer, and films could be cast from the solutions having the inherent viscosity as prepared. Alternately, the solution of the polymer can be concentrated by evaporation of the dioxane solvent without heating or the polymer can be isolated by precipitation by means of a non-solvent such as benzene. Then the precipitated polymer can be dissolved in an entirely different solvent and cast into films. However, if Brandt's solution, which already contains the polyamic acid, is treated with aqueous acids and alkalis as a method of isolating the polymer, the polymer is hydrolyzed to lower molecular weights incapable of forming films. Brandt (p. 164) used the diazo reaction of the amino group for the end-group determination on this acid-alkali-water isolated polymer and concluded that the hemiamic acid polymer contained eight to 10 blocks (units) in its linear chain. Since the diazo reaction is also performed in an aqueous solution with nitrous acid generated from hydrochloric acid and sodium nitrite, further degradation undoubtedly occurred in the determination. This sensitivity of amic acid polymers to hydrolysis by water has been noted in the polyamic acid of pyromellitimides and is similar to the sensitivity of phthalamic acids previously noted by M. L. Bender in JACS, 79, 1258 (1975).

EXAMPLE 6

In this example, 4-nitrophthalic anhydride was reduced by the procedure given by Brandt, cited in Example 5 above.

Three g of 4-nitrophthalic anhydride were dissolved in the hydrogenation apparatus (a 1.33% solution) in 300 ml of dioxane and after the addition of 0.59 g of Raney Nickel it was pressured with hydrogen to 250 psi and allowed to react at ambient temperature for 8 hours. The catalyst was removed from the solution by filtration and the solution concentrated at 20° C under 15 mm pressure, leaving a mixture of viscous oil containing some yellow powder. Filtration of the viscous oil through a sintered glass filter yielded 0.64 g of material which, when heated in a melting point tube from 25° C to higher temperatures, did not melt up to 300° C but gave evidence of decomposition in the range of 175°–180° C.

EXAMPLE 7

In 200 ml of dry ethyl ether, $(C_2H_5)_2O$, was dissolved 1.93 g of 4-nitrophthalic anhydride (~ 1% solution) to which was added 0.10 g of 5% palladium-on-charcoal and the mixture hydrogenated in a Paar hydrogenator at 39 psi at room temperature, until no more hydrogen was consumed. The catalyst was removed by filtration and the ether removed from the filtrate, maintained at 0° to −5° C, under vacuo, yielding a yellow crystalline solid mixed with non-crystalline viscous mass. When a small sample of this mixture was placed on a metal plate heated to 245° C, the product melted and polymerized immediately to a tough polymer. Extraction of the crystalline-non-crystalline mixture with ether left 0.46 g of polymer; concentration of the ether followed by cooling, yielded 0.86 g of 4-aminophthalic anhydride.

EXAMPLE 8

In 50 ml of freshly distilled deoxygenated N,N-dimethylformamide or N,N-dimethylacetamide containing 10 mg of 5% palladium-on-charcoal catalyst, there was dissolved 5.8 g (0.03 mole) of 4-nitrophthalic anhydride (~ a 10.6% solution) and the solution reduced with hydrogen at 40 psi while maintained at 20° C, until no more hydrogen was consumed, requiring approximately 90 minutes. The solution was then filtered through a sintered glass filter, the filtrate cooled to about 0° C and divided into two equal portions.

Portion A

One-half of the filtered solution was poured onto 200 g of very finely crushed ice with the formation of a bright yellow precipitate accompanied by the melting of the ice. The resulting water suspension was filtered rapidly, the precipitate isolated and dried, without heating, at 0.1 mm Hg pressure. The yield of dried product was 2.8 g (97%). It was not possible to record the infrared spectrum of the dried product as a KBr disc because of the reactivity of the 4-aminophthalic anhydride, since polymerization occurred when the product was ground with KBr or when the mixture of the product and KBr were molded into a disc prior to measurement. However, its infrared spectrum could be taken as a smear in Nujol; the product showed the complete disappearance of the $NO_2$ bands present in the precursor 4-nitrophthalic anhydride at 1540 cm$^{-1}$ and 1370 cm$^{-1}$, the retention of the anhydride bands at 1800 and 1725 cm$^{-1}$ and the appearance of the $NH_2$ band at 3330 cm$^{-1}$.

Analysis: Calc'd for $C_8H_5NO_3$; $NH_2C_6H_3(CO)_2O$: C, 58.90; H, 3.09; N, 8.59. Found: C, 58.86; H, 3.08; N, 8.57. Titration of a sample with 0.2 N NaOH established an equivalent weight of 163.1 compared to the theoretical value of 163 for product as dibasic acid anhydride.

The melting point of pure 4-aminophthalic anhydride could not be determined in the usual manner, either in a melting point tube or on a Fisher-Johns apparatus. When heating of the specimen was started at room temperature, the sample was not observed to melt even when heated to 300° C. When a sample was dropped on the preheated surface of the Fisher-Johns disc, melting was not observed at temperatures below 207° C, but it was observed to melt at 208° C and at higher temperatures to a clear yellow liquid which increased rapidly in viscosity during the course of which its color changed from a yellow to an orange to a brown solid film, which did not melt on further heating. This method of determining the melting point is referred to hereafter as the melt-no melt technique.

Portion B

The remaining half of the sample was concentrated at 15 mm Hg pressure without heat, leaving a viscous resinous mass. It was washed with a 50:50 mixture of toluene-methanol and finally with methanol, and dried at 50° C at 15 mm Hg pressure for 24 hours. There was obtained 4.61 g (94%) of a polymer whose infrared spectrum showed bands for COOH in the region of 3000 cm$^{-1}$, bands for CONH at 1660 cm$^{-1}$; weak bands for imide at 1765, 1725 and 725 cm$^{-1}$; weak bands for NH at 3330 cm$^{-1}$; and very weak bands for anhydride at 1800 cm$^{-1}$. The inherent viscosity of the resin in dimethylacetamide at 25° C was 0.26 dl/g.

The potentiometric titration of a sample with 0.2 N NaOH established that the polymer has one acid equivalent with an equivalent weight of 259.3. This value corresponds with a polymer containing a ratio of three segmers of hemiamic acid to two segmers of imide.

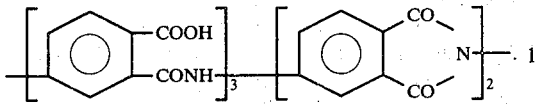

EXAMPLE 9

3-Nitrophthalic anhydride, 5.8 g, was 3: product isolated by the same procedure used to prepare its 4-isomer in Example 8. The yield was 94.6% and its melting point, determined by the melt-no melt technique used for the 4-isomer was 192° C.

Analysis: Calc'd for $C_8H_5NO_3$: C, 58.89; N, 3.09; N, 8.59. Found: C, 58.85; H, 3.07; N, 8.60.

Its infrared spectrum was similar to that of its 4-isomer; it did not show bands for $NO_2$ but did show bands for $NH_2$ in the 3330 cm$^{-1}$ region and for —CO—O—CO— in the 1800 and 1725 cm$^{-1}$ region.

EXAMPLE 10

A mixture of 3- and 4-nitrophthalic anhydride (5.8 g) was reduced and the product isolated by the procedure of Example 7. The yield was 95.1%, melting point determined by the melt-no melt technique ranged from 165 to 181° C. Its infrared spectrum showed the presence of bands for —$NH_2$ at 3300 cm$^{-1}$ and for —CO—O—OC— at 1800 and 1725 cm$^{-1}$ but no bands for $NO_2$.

Analysis: Calc'd for $C_8H_5NO_3$: C, 58.89; H, 3.09; N, 8.59. Found: C, 59.01; H, 3.10; N, 8.53.

EXAMPLE 11

In 50 ml of dry dioxane or tetrahydrofuran there was dissolved 1.93 g of 4-nitrophthalic anhydride and 0.10 g of 5% palladium-on-charcoal added and reduction with hydrogen at 56 psi performed at a temperature maintained at 15°-25° C in a shaking Paar apparatus until no more hydrogen was consumed. Then the solution was filtered to remove the catalyst. A sample of the solution was cast on glass and heated in an oven at 50° C for 24 hours, to yield a film which adhered to the glass; on additional heating, at 100° C for 24 hours, a hard film was obtained.

The remainder of the solution was poured onto 200 g of finely crushed ice with the formation of a yellow precipitate and partial melting of the ice. When most of the ice had melted, the precipitate was recovered by filtration and dried in vacuo at room temperature to constant weight to yield 1.4 g of product. When a sample of the product was slowly heated from room temperature to higher temperatures it did not melt, but when dropped on a metal block preheated to 210°-220° C, it melted to a thin melt and polymerized rapidly to a hard polymer. Its infrared spectrum and its elemental analysis of percent C, 58.82; H, 3.07; N, 8.56 confirms that this product was pure 4-aminophthalic anhydride and it is identical to the product prepared by the reduction performed in dimethylacetamide. The monomer was soluble also in diethyl ether, acetone, methanol, ethanol and benzene.

EXAMPLE 12

This example characterizes the differences in the thermal behavior of the pure isomeric 3- and 4-aminophthalic anhydrides.

A. 3-Aminophthalic Anhydride.

1. Differential Thermal Analysis. The sample was heated at a rate of 3° C/minute under nitrogen. A sharp endotherm, which peaked at 190° C, was observed; this temperature compares with 192° C found for its melting point by the melt-no melt technique reported hereinabove.

2. Thermogravimetric Analysis. The sample was heated at a rate of 3° C/minute under a nitrogen atmosphere at a flow of one standard liter per minute. Sublimation of the monomer was observed to begin at approximately 125° C and to condense on the surface of the gas-exit tube. Sublimation continued at a high rate to about 210° C, at which point reaction occurred and continued to about 300° C without further sublimation loss, after which water was eliminated to about 325° C; no further loss occurred on heating up to 500° C. In spite of the loss of sublimation of approximately 45%, there remained, after heating to 500° C, a polymeric residue amounting to approximately 40% by weight of the starting monomer.

B. 4-Aminophthalic Anhydride.

1. Differential Thermal Analysis

The sample was heated at a rate of 3° C/minute under nitrogen. A sharp endotherm which peaked at 207° C was observed; this temperature compares with 207°-208° C found for its melting point by the melt-no melt technique described hereinabove.

2. Thermogravimetric Analysis of Monomer

The sample was heated at a rate of 3° C/minute under a flow of nitrogen at one standard liter per minute. Sublimation of this 4- monomer did not occur as in the case of its 3- isomer. An inflection in the curve became evident in the range of 210°-241° C with a loss amounting to 11% at 315° C and 12% at 325° C, and 14% at 500° C. The calculated loss for the conversion of 4-aminophthalic anhydride to polyphthalimide is 11%. The char residue remaining at 500° C was 86%.

EXAMPLE 13

C. Mixed 3- and 4-Aminophthalic Anhydrides.

1. Differential Thermal Analysis a. An equal molar mixture of 3- and 4-aminophthalic anhydride was used in this test, following the same procedure as A.1 above. A broad exotherm was observed in the 170°-185° C region.

b. A sample of mixed anhydrides of Example 10 was treated by the procedure of A.1. A broad exotherm in the region of 158°-184° C was observed which compared to 160°-181° C found by the melt-no melt technique.

2. Thermogravimetric Analysis. The procedure described in A.1 was used.

a. An equal molar mixture of 3- and 4-aminophthalic anhydride was used. An inflection became evident at about 180° C with a loss amounting to about 12% at 315° C. Little or no sublimation was observed.

b. The mixed anhydride of Example 10 gave little or no evidence of sublimation and the behavior was similar to the synthetic mixture C.2.a above.

EXAMPLE 14

One g of 4-aminophthalic anhydride was dissolved in 50 ml of absolute ethanol and heated at 50° C for 3 hours, following which the alcohol was removed at 5–10 mm Hg pressure without heating, leaving as a crystalline solid the hemiester, m.p. 128° C; recrystallized from benzene, m.p. 131° C.

Analysis: Calc'd for $C_{10}H_{11}NO_4$ : C, 57.42; H, 5.30; N, 6.70. Found: C, 57.23; H, 5.32; N, 6.75.

EXAMPLE 15

In 100 ml of deoxygenated absolute alcohol in a Paar bottle there was dissolved 1.93 g of 4-nitrophthalic anhydride and 7 mg of 5% palladium-on-charcoal added. Then the apparatus was flushed with hydrogen and then pressured to 40.5 psi of hydrogen and the reduction allowed to continue for 12 hours at room temperature. Then the catalyst was removed by filtration and the filtrate concentrated at 10 mm Hg pressure at 25° C, leaving a residue which was recrystallized from benzene, m.p. 131° C. The mixed melting point with the sample of Example 14 was 130° C.

Analysis: Found: C, 57.13; H, 5.27; N, 6.71.

EXAMPLE 16

Solutions of pure 4-aminophthalic anhydride (AMPA) in dry, freshly distilled dioxane were prepared at room temperature and then were concentrated to constant weight at 15 mm Hg pressure without heat. In all cases, viscous resinous masses were obtained which were extracted with benzene in which the monomer is soluble and the polymer insoluble. Concentration of the benzene extract to dryness gives values reported as the monomer, the difference is reported as polymer (or oligomer). The data are shown in Table 1.

Table 1

| Solution | 4-AMPA g | Dioxane g | % Wt. AMPA | % Products Polymer | % Products AMPA |
|---|---|---|---|---|---|
| A | 1 | 99 | 1 | 77 | 23 |
| B | 1 | 19 | 5 | 88 | 12 |
| C | 1 | 9 | 10 | 100 | 0 |
| D | 1 | 3 | 25 | 100 | 0 |
| E | 1 | 2 | 33⅓ | 100 | 0 |

Similar results are obtained when solutions of AMPA are prepared in low boiling solvents such as tetrahydrofurane and ethyl acetate, but in the higher boiling solvents such as 1 and 5% by weight solutions in DMF and DMAC, respectively, evaporation of these solvents at room temperature, leaves only 2 and 1% unconverted 4-AMPA respectively.

EXAMPLE 17

Solutions of 3-aminophthalic anhydride are prepared in dioxane and concentrated by the procedure of Example 6 and the data are given in Table 2.

Table 2

| Solution | Weight % of 3-AMPA | % Products Polymer | % Products Monomer |
|---|---|---|---|
| A | 1 | 70 | 30 |
| B | 5 | 82 | 18 |
| C | 10 | 98 | 2 |
| D | 25 | 100 | 0 |

Table 2-continued

| Solution | Weight % of 3-AMPA | % Products Polymer | % Products Monomer |
|---|---|---|---|
| E | 33⅓ | 100 | 0 |

The data indicate 3-AMPA is less reactive than 4-AMPA. In DMAC or DMF, the 1 and 5 weight percent solutions yield only 8 and 6% unreacted 3-AMPA, respectively, on evaporation of the solvent compared to 2 and 1 percent respectively for 4-AMPA.

EXAMPLE 18

Solutions of equal molar portions (1:1) of 4-AMPA and 3-AMPA are prepared in dioxane and concentrated by the procedure of Example 16 and the data are given in Table 3.

Table 3

| Solution | Weight % of 1:1 anhydrides | % Products Polymer | % Products Monomer |
|---|---|---|---|
| A | 1 | 76 | 24 |
| B | 5 | 86 | 14 |
| C | 10 | 100 | 0 |
| D | 25 | 100 | 0 |
| E | 33 | 100 | 0 |

In the DMAC or DMF the 1 and 5% by weight solutions, respectively, leave, on evaporation of the solvent, 2.3 and 1.0% of unconverted anhydrides.

EXAMPLE 19

The following example illustrates the use of aromatic diamines, $NH_2—Ar—NH_2$, or aromatic tetracarboxylic acid dianhydrides,

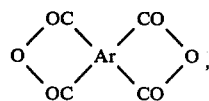

as modifiers in the polymerization of 4-AMPA. Solutions of 1.63 g of 4-AMPA were prepared in DMAC at room temperature, and the modifier, when used, was then added to the amount of a molar ratio of 1 mole of modifier to 100 moles of 4-AMPA and the polymerization conducted at 70° C for 8 hours, and the inherent viscosity of the modified polymers was measured as 0.5% solution in DMAC. The data are summarized in Table 4.

Table 4

| Solution | Modifier* g | DMAC ml | Weight % Solid | $\eta$ inh Polymer |
|---|---|---|---|---|
| A | none | 5 | 25 approx. | 0.310 |
| B | PMA;0.022 | 5 | 25 approx. | 0.481 |
| C | MPD;0.011 | 5 | 25 approx. | 0.442 |
| D | PMA;0.022 | 3.37 | 33 approx. | 0.600 |
| E | MPD;0.011 | 3.37 | 33 approx. | 0.561 |

*PMA is pyromellitic anhydride
MPD is meta-phenylenediamine

The inherent viscosity of the modified polymers is substantially higher than the unmodified products. Corresponding improvements in inherent viscosity are obtained when instead of PMA there is used benzophenone tetracarboxylic acid dianhydride, or instead of MPD there is used p-phenylenediamine, oxydianiline, methylene dianiline, sulfonyl dianiline, $H_2NC_6H_4(OC_6H_4)_2NH_2$, $(H_2NC_6H_4OC_6H_4)_2SO_2$, and other ratios are used, such as in the range of 100 to 1000 moles of the aminophthalic anhydride per mole of diamine or dianhydride modifier respectively.

EXAMPLE 20

This example illustrates the improvement in the inherent viscosity when the modifier is introduced into a hydrogenation system before the 4-nitrophthalic anhydride is reduced to the 4-AMPA and polymerization allowed to occur simultaneously with hydrogenation.

(a) To a solution in a hydrogenation vessel of 19.3 g of 4-nitrophthalic anhydride in 38.6 g of DMAC was added 0.50 g of 5% palladium-on-charcoal catalyst and the mixture pressured with hydrogen to 75 psi heated to 60° C. Agitation was started and an exotherm raised the temperature to 70° C where it was maintained during the course of 8 hours. The mixture was then cooled to 20°-25° C and filtered to remove the catalyst, yielding a viscous filtrate. The inherent viscosity was 0.41 measured as a 0.5% by weight solution in DMAC at 30° C.

(b) To a solution in a hydrogenation vessel of 19.3 g of 4-nitrophthalic anhydride and 0.22 g of pyromellitic anhydride in 38.6 g of DMAC was added 0.52 g of 5% palladium-on-charcoal catalyst and the mixture hydrogenated as in (a) above. The inherent viscosity was 0.63.

(c) To 38.6 g of DMAC there was dissolved 0.11 g of m-phenylenediamine, then 19.3 g of 4-nitrophthalic anhydride was added, followed by 0.51 g of 5% palladium-on-charcoal and the mixture hydrogenated as in (a) above. The inherent viscosity was 0.56. Substantially identical results are obtained if, instead of m-phenylenediamine, an equivalent amount of meta or para dinitrobenzene, 0.168 g, are used and reduced in situ.

Continuous films were obtained by the casting of these solutions on plates and drying at 130° C. The films from (b) and (c) were much tougher than the film from (a).

(d) Procedures (a), (b) and (c) above were repeated in the presence of 7 g of anhydrous magnesium sulfate, and solution having at least a 5% higher viscosity were obtained, 0.456, 0.701 and 0.622 dl/g respectively.

EXAMPLE 21

To establish that the modifiers of Example 19 function as coupling agents to increase the viscosity, Example 19 was repeated twice, using instead of MPD an equivalent amount of the precondensed product of the formula

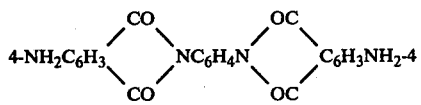

prepared by two independent methods, A and B, yielding substantially identical results to those obtained in Example 19.

Method A.

Two moles of 4-nitrophthalic anhydride and one mole, as a 10% solution, of MPD, were dissolved in glacial acetic acid, then three moles of acetic anhydride were added and the mixture heated at 100° C for 4 hours, cooled to room temperature, poured onto crushed ice, filtered and dried, to yield

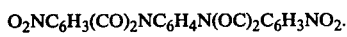

Then 4.58 parts of the dinitro- compound were dissolved in 50 parts of DMAC and reduced catalytically at 20° C by the procedure of Example 8.A, to give

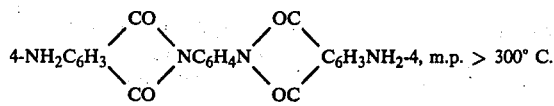

The elemental analysis percent C, 66.35; H, 3.5; N, 14.07 and 0, 16.14 is in good agreement with the theoretical values.

Method B

To a solution of 10.8 g of MPD in 100 ml of m-cresol and 15 ml of benzene, there was added 32.6 g of 4-aminophthalic anhydride, and the mixture reacted at reflux in a flask connected to a Dean-Stark trap until no more water was collected. Then the mixture was concentrated under vacuum, washed with benzene and dried. Its elemental analysis percent, C, 66.33; H, 3.51; N, 14.04; 0, 16.08 is in very good agreement with the compound of Method A.

EXAMPLE 22

The procedure of Example 21.B was used to react 1 mole of PMA and 10mole of AMPA by the benzene:m-cresol azeotropic process of Example 21.B to give

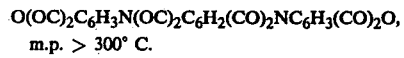

m.p. > 300° C.

Analysis: Calc'd for C, 61.42; H, 1.57; N, 5.51. Found: C, 62.01; H, 1.61; N, 5.46.

This precondensed product, when used in Example 19, instead of PMA, in an equivalent amount, yields polymers with properties substantially equivalent to those in which the PMA is not precondensed with AMPA.

EXAMPLE 23

An amine end-capped oligomeric polyimide (AEO-1) was prepared as follows: In a m-cresol:benzene azeotropic apparatus of Example 21.B was placed BTCA* (11.2781 g, 0.035 mole), SDA-3,3** (10.8760 g, 0.0438 mole), 80 ml of m-cresol and 10 ml of benzene. The ratio of BTCA-SDA-3,3 is 4:5. The mixture was refluxed for 3½ hours, during which time 1.3 ml of water was collected. Then, the benzene was distilled off and the solution was precipitated in methanol. The precipitated oligomer was digested three times in hot methanol and then vacuum dried at 70° C for 24 hours to give 19.7498 g (95%) as a light-yellow solid which was soluble in m-cresol, DMAC and sulfolane; it swelled in hot dioxane and melted at 245°-280° C. A sample was vacuum-dried at 200° C and analyzed.

Analysis: Calc'd for $C_{128}H_{68}N_{10}O_{30}S_5$: C, 64.42; H, 2.87; N, 5.87; O, 20.12; S, 6.72. Found: C, 63.71; H, 2.91; N, 5.75; O, ---; S, ---.

\* BTCA is 3,3',4,4'-benzophenonetetracarboxylic acid dianhydride.
\*\* SDA-3,3 is 3,3'-sulfonyldianiline.

EXAMPLE 24

An amine end-capped oligomeric polyimide (AEO-2) was prepared as follows: According to the procedure given in Example 23, there was allowed to react BTCA (11.2781 g, 0.035 mole) and SDA-3,3 (9.7834 g, 0.0394 mole) in 80 ml of m-cresol and 10 ml of benzene. The ratio of SDA-3,3 to BTCA is 9:8. There was obtained the oligomer, AEO-2, as a light-yellow solid, 18.3 g (92.5%), which was soluble in m-cresol, DMAC and sulfolane. It swelled in hot dioxane. On a Fisher-Johns apparatus it melted partially at 255° C. The lowest temperature at which a sample would melt completely when dropped onto the preheated block was 280° C. The analysis was performed on a small sample vacuum-dried at 200° C.

Analysis: Calc'd for $C_{244}H_{124}N_{18}O_{58}S_9$: C, 64.77; H, 2.76; N, 5.57; O, 20.51; S, 6.38. Found: C, 63.54; H, 2.81; N, 5.45; O, ----; S, ----.

EXAMPLE 25

An amine end-capped oligomeric polyimide (AEO-3) was prepared as follows: According to the procedure given in Example 23, BTCA (3.2223 g, 0.01 mole) and DAPB-3,3* (3.6529 g, 0.0125 mole) were allowed to react. The ratio of BTCA to DAPB-3,3 is 4:5. There was obtained 6.1215 g (94%) of AEO-3 as a yellow powder which, on a Fisher-Johns melting point apparatus melted in the range of 180°-200° C. It was soluble in m-cresol, DMAC, sulfolane and dioxane.

Analysis: Calc'd for $C_{158}H_{88}N_{10}O_{30}$: C, 72.81; H, 3.40; N, 5.37; O, 18.42. Found: C, 72.72; H, 3.35; N, 4.77; O, ----.

* DAPB-3,3 is 1,3-di(3-aminophenoxy)benzene.

EXAMPLE 26

An amine end-capped oligomeric polyimide (AEO-4) was prepared as follows: According to the procedure given in Example 23, BTCA (3.2223 g, 0.01 mole) and DAPB-3,3 (3.2887 g, 0.01125 mole) were allowed to react. The ratio of BTCA to DAPB-3,3 is 8:9. There was obtained AEO-4 as a yellow powder, 5.8708 g (95.4%). On a Fisher-Johns apparatus it began to melt at 190° C but did not melt completely by 200° C. The lowest temperature at which a sample melted when dropped onto a preheated block was 220° C. It was soluble in m-cresol, DMAC, sulfolane and dioxane.

Analysis: Calc'd for $C_{298}H_{160}N_{18}O_{58}$: C, 72.74; H, 3.28; N, 5.12; O, 18.86. Found: C, 72.45; H, 3.31; N, 5.04; O, ----.

EXAMPLE 27

An anhydride end-capped oligomeric polyimide (ANEO-1) was prepared as follows: According to the procedure of Example 23, there was allowed to react BTCA (12,0837 g, 0.0375 mole) and SDA-3,3 (7.4493 g, 0.03 mole) in 80 ml of m-cresol and 10 ml of benzene. The ratio of BTCA to SDA-3,3 is 5:4. There was obtained the oligomer ANEO-1, as a light-yellow solid, 16.9 g (92%) which was soluble in m-cresol, DMAC, DMF and sulfolane. It softened at 240° C and melted from 245°-265° C.

Analysis: Calc'd for $C_{133}H_{62}N_7O_{35}S_4$: C, 65.30; H, 2.56; N, 4.01; O, 22.89; S, 5.24. Found: C, 63.90; H, 2.74; N, 4.70; O, ----; S, ----.

EXAMPLE 28

An anhydride end-capped oligomeric polyimide (ANEO-2) was prepared as follows: According to the procedure of Example 23, there was allowed to react BTCA (14.5003 g, 0.045 mole) and SDA-3,3 (9.9324 g, 0.04 mole) in 90 ml of m-cresol and 20 ml of benzene. The ratio of BTCA to SDA-3,3 is 9:8. There was obtained the oligomer, ANEO-2, as a light-yellow solid, 21.4 g (95%) which was soluble in m-cresol, DMAC, DMF and sulfolane. It melted partially at 265° C. The lowest temperature at which a sample melted completely when dropped onto a preheated block was 270° C.

Analysis: Calc'd for $C_{249}H_{118}N_{15}O_{63}S_8$: C, 65.24; H, 2.60; N, 4.58; O, 11.99; S, 5.60. Found: C, 63.99; H, 2.73; N, 4.95; O, ----; S, ----.

EXAMPLE 29

An anhydride end-capped oligomeric polyimide (ANEO-3) was prepared as follows: According to the procedure of Example 23, there was allowed to react BTCA (4.0279 g, 0.0125 mole) and DAPB-3,3 (2.9223 g, 0.01 mole) in 40 ml of m-cresol and 10 ml of benzene. The ratio of BTCA to DAPB-3,3 is 5:4. There was obtained the oligomer ANEO-3 (5.7678 g, 80%) as a light-yellow powder which was soluble in m-cresol, DMAC, sulfolane and dioxane. On a Fisher-Johns melting point apparatus it melted over the range of 190°-205° C.

Analysis: Calc'd for $C_{157}H_{78}N_8O_{35}$: C, 71.52; H, 2.98; N, 4.25; O, 21.24. Found: C, 71.41; H, 3.21; N, 4.46; O, ----.

EXAMPLE 30

An anhydride end-capped oligomeric polyimide (ANEO-4) was prepared as follows: According to the procedure of Example 23 there was allowed to react BTCA (3.6251 g, 0.01125 mole) and DAPB-3,3 (2.9223 g, 0.01 mole) in 40 ml of m-cresol and 10 ml of benzene. The ratio fo BTCA to DAPB-3,3 is 9:9. There was obtained ANEO-4 (5,6071 g, 90%) as a light-yellow powder which was soluble in m-cresol, DMAC, sulfolane and dioxane. On a Fisher-Johns melting point apparatus it melted in the range of 185°-215° C.

Analysis: Calc'd for $C_{297}H_{150}N_{16}O_{63}$: C, 72.04; H, 3.09; N, 4.53; O, 10.35. Found: C, 71.09; H, 3.22; N, 4.60; O, ----.

EXAMPLE 31

A 5 ml solution of Polymer B of Example 19 was mixed with a 5 ml solution of Polymer C of Example 19 and allowed to stand at 25° C for 6 hours. Coupling of the anhydride-terminated Polymer B with the amine-terminated Polymer C occurred, yielding a product, with an inherent viscosity of 0.583 dl/g in a 0.5% solution of DMAC.

Similarly, equivalent weights of Polymers D and E of Example 19, coupled when mixed, to increase the inherent viscosity of 0.674 dl/g.

EXAMPLE 32

Equal molar amounts of the amine-terminated pimer of Example 21A and of the anhydride-terminated dimer of 22A are first prepared as 30% solutions in DMAC and then mixed at 20° C to yield a block polyimide-polyamic acid, inherent viscosity 0.469 dl/g of the structure

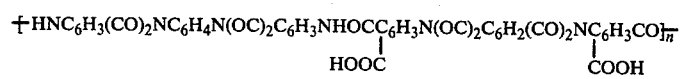

EXAMPLE 33

The oligomer AEO-1 of Example 23 (2.384 g) is dissolved in 10 ml of DMAC and there is slowly added 1.63 g of AMPA, yielding a clear, viscous solution of a polymer which can be generalized by the formula

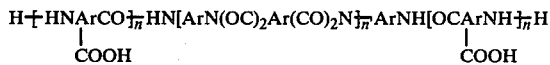

in which n' is 4 and n is 5.

In a similar way, instead of AEO-1, 4.28 g of AEO-2 of Example 24, 2.718 g of AEO-3 of Example 25 and 4.915 g of AEO-4 of Example 26, respectively, are reacted with 1.63 g of AMPA. In the case of AEO-2 and AEO-4, the value of n' is 8. When 3.26 g of AMPA are used in the above reactions, the value of n is 10.

EXAMPLE 34

The procedure of Example 26 is repeated and when the initial condensation for AEO-4 is completed, 1.63 of AMPA is added and the reaction continued until no more water is collected in the water trap and there is obtained a completely cyclized block-polyimide instead of the hemiamic acid form shown in Example 33, which can be represented by

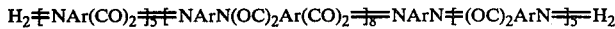

The same procedure, using AEO-1, AEO-2 and AEO-3 instead of AEO-4, yields compounds conforming to the above structure with the appropriate values of n' and n; the value of n depending on the amount of AMPA used.

EXAMPLE 35

The oligomer ANEO-1 of Example 27 (2.444 g) is dissolved in 10 ml of DMAC and 1.63 g of AMPA added and reacted as in Example 33, to yield a clear, viscous solution of polymer which can be generalized by the formula:

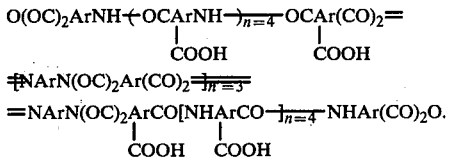

In a similar way, instead of ANEO-1, 4.585 g of ANEO-2 of Example 28; 2.634 g of ANEO-3 of Example 29, and 4.946 g of ANEO-4 of Example 30, respectively, are reacted with 1.63. g of AMPA wth the appropriate values of n' and n, in which the value of n' is determined by the values in the ANEO-oligomers and n by the amount of AMPA reacted. When 3.26 g of AMPA is used, the value of n is 9.

EXAMPLE 36

The procedure of Example 30 is repeated and when the initial condensation for ANEO-4 is completed, 1.63 g of AMPA is added and the reaction continued until no more water is collected and there was obtained a completely cyclized block polyimide instead of the hemiamic acid form shown in Example 35, which can be written

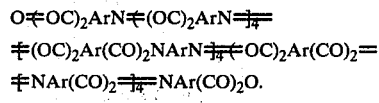

Similarly, ANEO-1, ANEO-2 and ANEO-3 can be condensed with AMPA to produce completely cyclized block polyimides.

EXAMPLE 37

Similar results are obtained when the procedure of Example 5A is repeated a number of times using individually in place of the 4-nitrophthalic anhydride equivalent amounts respectively of 3-nitro-4fluoro-phthalic anhydride,
4-nitro-5-chloro-phthalic anhydride,
3-nitro-5-bromo-phthalic anhydride,
3-nitro-4-butyl-phthalic anhydride.

As will be evident to those skilled in the art, various modifications of this invention can be made or followed in the light of the foregoing disclosure without departing from the spirit or scope of this invention.

What is claimed is:

1. The process of preparing a modified film-forming polyamic acid which comprises reacting an aminophthalic acid of the formula $H_2NC_6H_nY_{3-n}(CO)_2O$ wherein Y represents a halogen selected from the group consisting of F, Br and Cl, and n represents an integer having a value of 0 to 3, in an inert organic solvent in which the polymer is soluble, at a temperature of about 10°–100° C with 0.5 to 0.001 mole, per mole of the aminoanhydride, of a compound having the formula $Ar(CO)_2 O_2$, in which Ar represents single, fused and heterocyclic aromatic rings, said heterocyclic rings being selected from the class consisting of pyridine quinoline and quinoxaline, and a multiplicity of such rings linked to each other directly or by —O—, —S—, —CO—, —SO$_2$—, —CR$_2$—, —NR—,

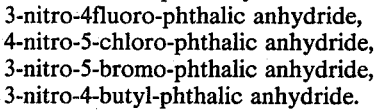

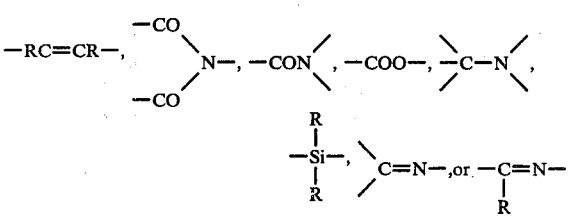

linkages in which R represents hydrogen or a hydrocarbon group containing one to twelve carbon atoms, and the remaining positions in the Ar groups being occupied by hydrogen and a halogen selected from the class consisting of F, Cl and Br.

2. The process of claim 1 in which the modifier is $O(CO)_2C_6H_3COC_6H_3(CO)_2 0$.

3. The process of claim 1 in which the modifier is $O(CO)_2C_6H_2(CO)_2 0$.

4. The film-forming polyamic acid which consists of the reaction product of an aminophthalic anhydride of the formula $H_2NC_6H_nY_{3-n}(CO)_2O$ wherein Y represents a halogen selected from the class consisting of F, Br and Cl, and n represents an integer having a value of 0 to 3, and about 0.1 to 0.001 mole of a compound having the formula Ar $((CO)_2O)_2$ in which AR represents single, fused and heterocyclic aromatic rings, said heterocyclic rings being selected from the class consisting of pyridine, quinoline and quinoxaline, and a multiplicity of such rings linked to each other directly or by —O—, —S—, —CO—, $SO_2$—, —$CR_2$—, —NR—, —RC=CR—,

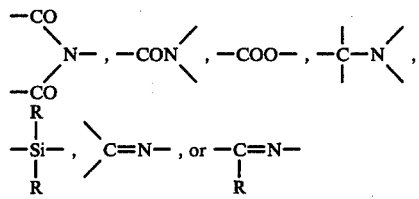

linkages in which R represents hydrogen or a hydrocarbon group containing one to twelve carbon atoms, and the remaining positions in the Ar groups being occupied by hydrogen or a halogen selected from the class consisting of F, Cl and Br 5. The process of claim 1 which comprises reacting at least 5 moles of said aminophthalic anhydride with one mole of said compound having the formula Ar.

6. The process of claim 5 in which said aminoanhydride is 4-aminophthalic anhydride.

7. The process of claim 5 in which said aminoanhydride is 3-aminophthalic anhydride.

8. The process of claim 5 in which a mixture of 3- and 4-aminophthalic anhydride is used as the aminoanhydride.

9. The process of claim 8 in which the relative proportions 3- and 4-aminophthalic anhydrides corresponds to the quantity obtained by the reduction of the mixture of nitrophthalic anhydrides obtained by the nitration of phthalic anhydride.

10. The process of claim 5 in which 5 to 1000 moles of said aminophthalic anhydride are used per mole of said Ar $((CO)_2O)_2$ compound.

11. The dianhydride-terminated polymer produced by the process of claim 10.

12. The process of claim 5 in which meta-cresol comprises a major portion of the solvent.

13. The process of claim 5 in which an N,N-dimethyl acylamide comprises a major portion of the solvent.

14. The process of claim 5 in which N-methyl pyrrolidone comprises a major portion of the solvent.

15. The process of claim 5 in which an aromatic hydrocarbon of the formula $C_6H_3R'_3$, wherein R' represents hydrogen or methyl, comprises a major portion of the solvent.

* * * * *

UNITED STATES PATENT OFFICE
CERTIFICATE OF CORRECTION

Patent No. 4,131,730　　　　　　Dated　December 26, 1978

Inventor(s)　Gaetano F. D'Alelio

It is certified that error appears in the above-identified patent and that said Letters Patent are hereby corrected as shown below:

Col.24, line 38, correct $Ar(CO)_2O_2$ to read $Ar((CO)_2O)_2$

Col.25, line 1, correct AR to read Ar

Col. 25, line 24, correct Ar to read -- $Ar_2$ --.

Signed and Sealed this

Tenth Day of April 1979

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,131,730

DATED : December 26, 1978

INVENTOR(S) : Gaetano F. D'Alelio

It is certified that error appears in the above—identified patent and that said Letters Patent are hereby corrected as shown below:

Column 24, line 38, "$Ar(CO)_2O_2$" should read -- $Ar((CO)_2O)_2$ --.

Column 25, line 1, "AR" should read -- Ar --.

Column 25, line 24, "Ar" should read -- $Ar((CO)_2O)_2$ --.

This supersedes Certificate of Correction dated April 10, 1979.

Signed and Sealed this

Twenty-fourth Day of July 1979

[SEAL]

Attest:

Attesting Officer

LUTRELLE F. PARKER
Acting Commissioner of Patents and Trademarks